United States Patent [19]

Block et al.

[11] Patent Number: 5,478,959
[45] Date of Patent: Dec. 26, 1995

[54] METHOD FOR PREPARING 1,2-DITHIINS AND PRECURSORS OF 1,2-DITHIINS

[75] Inventors: Eric Block, Schenectady, N.Y.; Chuangxing Guo, West Lafayette, Ind.

[73] Assignee: The Research Foundation of State University of New York, Albany, N.Y.

[21] Appl. No.: 318,504

[22] Filed: Oct. 5, 1994

[51] Int. Cl.$^6$ .......................... C07F 7/22; C07C 327/18; C07C 323/05; C07C 323/22
[52] U.S. Cl. ................. 556/87; 568/39; 568/41; 568/56; 568/57; 558/252
[58] Field of Search ................. 568/34, 42, 56, 568/57, 87; 558/252

[56] References Cited

U.S. PATENT DOCUMENTS

| | | | |
|---|---|---|---|
| 2,061,019 | 11/1936 | Carter et al. | 568/57 |
| 3,096,375 | 7/1963 | Campbell et al. | 568/57 |
| 5,202,348 | 4/1993 | Towers et al. | 514/436 |

FOREIGN PATENT DOCUMENTS 117495  4/1958  U.S.S.R.

OTHER PUBLICATIONS

Schroth et al., "1,2-Dithiins, a New Type of Heterocycle", vol. 6, No. 8 pp. 649–722, Aug. 1967, Angew. Chem, Int. Ed.
Towers et al. "Antibiotic Properties of Thiaurbrine A, a Naturally . . . " *Planta Medica*, 225–229 (1985).
Eisner et al. "Recent Developments in the Chemistry of o– and m–Dithiins" *Int. J. Sulfur Chem.*, B, 7, 101–107 (1972).
Hartke et al. "Eigenschaften und Reaktionen der Thiobernstein–und Thioglutarsäureester" *Liebigs Ann. Chem.*, 933–941 (1988).
Koreeda et al. "The Chemistry of 1,2–Dithiins: Synthesis of 1,2–Dithin and 3,6–Disubstituted . . . " *Synlett*, 201–203 (1994).
Zhang et al. "Palladium–and Molybdenum–Catalyzed Hydrostannation of Alkynes. A Novel Access . . . " *J. Org. Chem.*, 55: 1857–1867 (1989).
Margiotis et al. "A Novel Approach to the Synthesis of Enediynes" *Tetrahedron Letters* 32, 6085–6088 (1991).
Magriotis et al. "A Highly Selective Synthesis of Versatile (E)–1–Phenylthio Vinystannanes" *Tetrahedron Letters* 32, 5047–5050 (1991).

*Primary Examiner*—Glennon H. Hollrah
*Assistant Examiner*—Mary C. Cebulak
*Attorney, Agent, or Firm*—Heslin & Rothenberg

[57] ABSTRACT

A method for preparing 1,4-(Z,Z)-disubstituted-1,4-disulfurated-1,3-butadienes is disclosed. The butadienes can be further elaborated to provide 3,6-unsymmetrically-substituted-1,2-dithiins. Also disclosed are butadienes prepared by the method of the invention. These butadienes are useful as intermediates in the synthesis of antibiotic 1,2-dithiins.

7 Claims, No Drawings

METHOD FOR PREPARING 1,2-DITHIINS AND PRECURSORS OF 1,2-DITHIINS

STATEMENT OF RIGHTS UNDER FEDERALLY SPONSORED RESEARCH

This invention was made with support under the NRI Competitive Grants Program/USDA (Award No. 92-37500-8068) and NSF Grant No. CHE9303866. Accordingly, the U.S. Government has certain rights in the invention.

BACKGROUND OF THE INVENTION

Giant ragweed (*Ambrosia trifida*), used in herbal medicine as an antiseptic and to treat intestinal worms and fever, contains significant quantities (ca. 0.003% by weight) of 3-(3-buten-1-ynyl)-6-(1,3-pentadiynyl)-1,2-dithiin (thiarubrine B), and lesser quantities of 3-(5 hexen-1,3-diynyl)-6-(1-propynyl)-1,2-dithiin (thiarubrine A) and related compounds. Thiarubrines are notable as a class of light-sensitive, biologically potent, structurally unique polyacetylenic plant pigments containing an antiaromatic 8π-electron 1,2-dithiin ring system. First identified in 1964–65 in species of Compositae (Asteraceae) used for skin infections and intestinal parasites by native people in Africa and Canada, thiarubrines show good light-mediated activity against human immunodeficiency virus (HIV-1) and possess significant antibiotic, antiviral and nematicidal activity both in the light and in the dark. Ten 3,6-disubstituted 1,2-dithiins have so far been identified in nature, including some with epoxide, alcohol, or chloro groups, as well as a 1,2-dithiin 1-oxide.

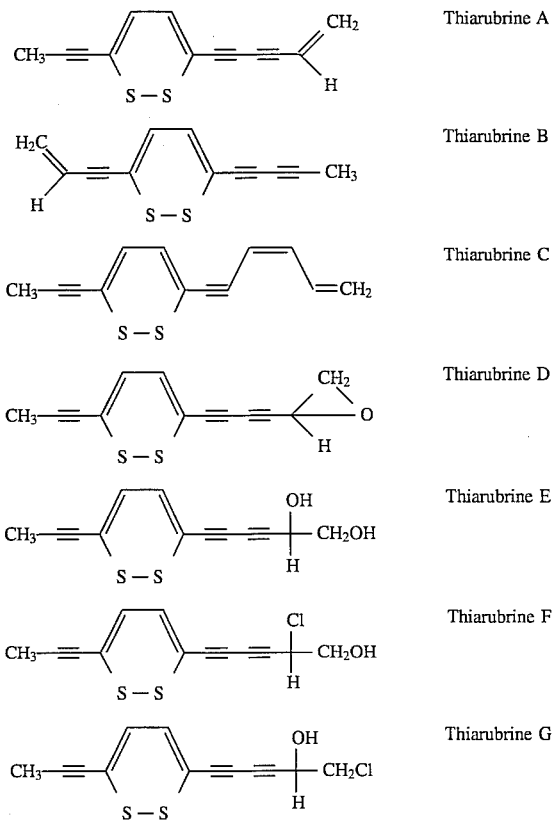

Thiarubrine A
Thiarubrine B
Thiarubrine C
Thiarubrine D
Thiarubrine E
Thiarubrine F
Thiarubrine G

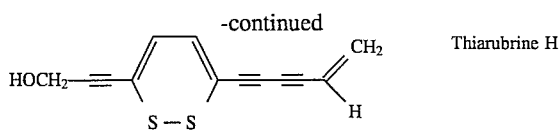

Thiarubrine H

In addition a monosubstituted (at ring position 3) 1,2-dithiin has also been identified from a North African medicinal plant.

Two groups have reported syntheses of simple 1,2-dithiins that could be considered models for thiarubrines, but in the 30 years since their discovery, no chemical syntheses of the natural products have been reported. The absence of a flexible chemical synthesis hampers detailed study of the biological activity and chemical and physical properties of thiarubrines. There is therefore a need for a chemical synthesis of 1,2-dithiins that allows wide flexibility in the substituents at positions 3 and 6.

SUMMARY OF THE INVENTION

The process of the invention provides a total synthesis of thiarubrine B, by a route which permits ready synthesis of the other members of this remarkable class of natural products as well as a variety of symmetrical and unsymmetrical homologs, desirable for biological testing. This route creates the S—S bond of the dithiin following elaboration of the residues that will become the substituents at positions 3 and 6 of the ultimate 1,2-dithiin, thereby minimizing the synthetic disadvantages that arise from the instability and reactivity of the 1,2-dithiin ring system.

In one aspect the invention relates to a method for preparing an unsymmetrically substituted 1,4-disulfurated-1,3-butadiene comprising the sequential steps of: (a) reacting a 1,4-disulfurated-1,3-butadiyne with a triaryl or trialkylstannane to form a 1,4-disulfurated-1,4-distannyl-1,3-butadiene; and (b) treating the 1,4-disulfurated-1,4-distannyl-1,3-butadiene with iodine, bromine or chlorine to produce a 1,4-disulfurated-1-halo-4-stannyl-1,3-butadiene. By the term "disulfurated" is meant that the butadiene or butadiyne contains two sulfur-containing substituents attached to the butadiene or -yne through the sulfurs. The bonding in such compounds would include them in the class of thioethers. For example, compounds of formula:

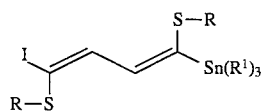

wherein R is any group suitable for protecting a thiol and $R^1$ is alkyl of 1 to 4 carbons or phenyl, would fall within the class of "disulfurated" butadienes.

A generic depiction of the process of the first aspect of the invention would be:

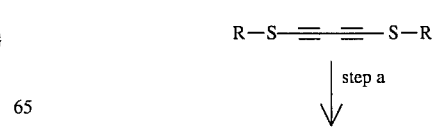

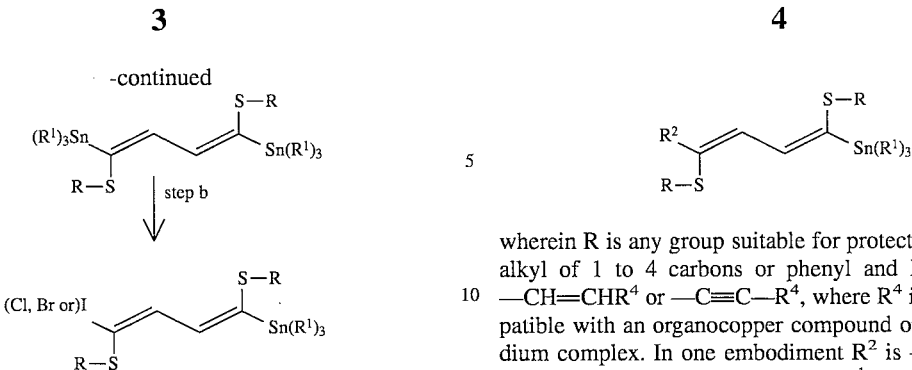

In this, as in all subsequent schemes containing structural formulae, the substituent groups are defined when introduced and retain that definition throughout the specification and claims. The term "alkyl" as used herein refers to linear, branched or cyclic saturated hydrocarbons of ten or fewer carbons.

In a preferred method a 1,4-disulfurated-1,3-butadiyne is reacted with a triaryl or trialkylstannane in the presence of a catalyst chosen from the group consisting of palladium complexes, trialkylboron compounds and combinations of the two. The 1,4-disulfurated-1,3-butadiyne may be 1,4-bis(benzylthio)-1,3-butadiyne. In a preferred embodiment the triaryl or trialkylstannane is triphenyltin hydride, the catalyst is a combination of tetrakis(triphenylphosphine)palladium(0) plus triethyl boron, and the 1,4-disulfurated-1-halo-4-stannyl-1,3-butadiene is 1,4-bis(benzylthio)-1-iodo-4-(triphenylstannyl)-1,3-butadiene.

The method above may be further extended to include the additional step of treating the 1,4-disulfurated-1-halo-4-stannyl-1,3-butadiene with a copper-palladium complex or copper complex of a first substituent residue whereby a 1,4-disulfurated-4-stannyl-1,3-butadiene having the substituent residue at position 1 is formed. A generic description of the process including the additional step would be:

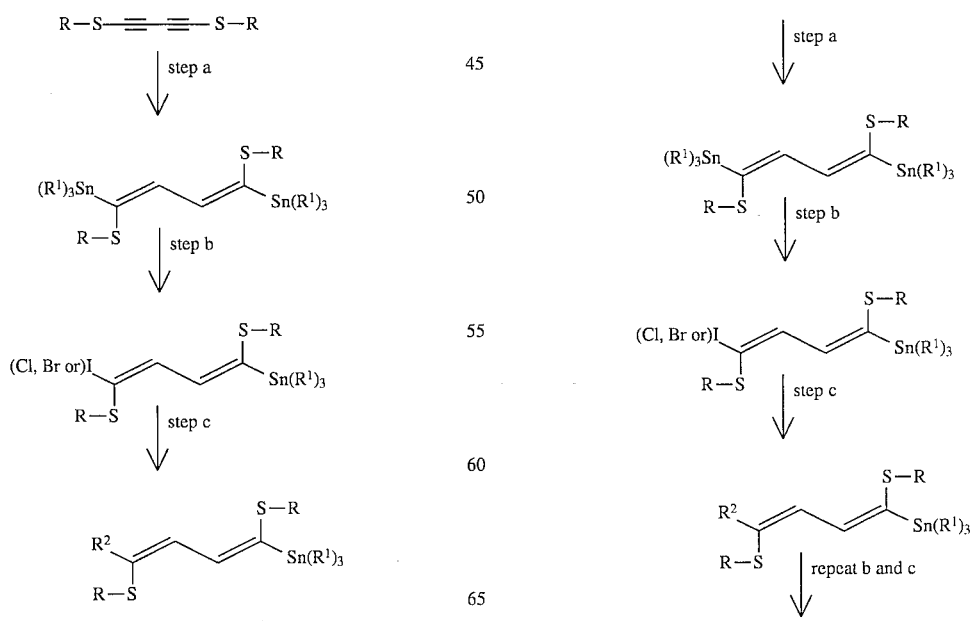

In this manner one can prepare compounds of formula:

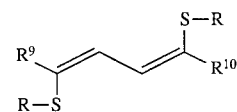

wherein R is any group suitable for protecting a thiol; $R^1$ is alkyl of 1 to 4 carbons or phenyl and $R^2$ is —$CH_2R^4$, —CH=CHR$^4$ or —C≡C—$R^4$, where $R^4$ is a residue compatible with an organocopper compound or a copper-palladium complex. In one embodiment $R^2$ is —C≡C—$R^4$. In another embodiment R is benzyl, $R^1$ is phenyl and $R^2$ is —C≡C—Si(CH$_3$)$_3$. The copper-palladium complex may be derived from a terminal acetylene, copper iodide and bis-(triphenylphosphine)palladium(II) chloride.

The method described above can further include the additional steps of (a) treating the 1,4-disulfurated-4-stannyl-1,3-butadiene having a first substituent residue at position 1 with iodine, bromine or chlorine to produce a 1,4-disulfurated-4-halo-1-substituted-1,3-butadiene; and (b) treating the resulting 1,4-disulfurated-4-halo-1-substituted-1,3-butadiene with a copper-palladium complex or a copper complex of a second substituent residue whereby a 1,4-disulfurated-1,3-butadiene having first and second substituent residues at positions 1 and 4, respectively, is formed. By this method one can make compounds of formula:

wherein $R^9$ is —CH=CHR$^{4a}$ or C≡C—$R^{4a}$; $R^{10}$ is —CH=CHR$^{4b}$ or C≡C—$R^{4b}$; and $R^{4a}$ and $R^{4b}$ are trimethylsilyl or a $C_1$ to $C_{10}$ hydrocarbon. A generic representation of the overall process, including the additional steps, would be:

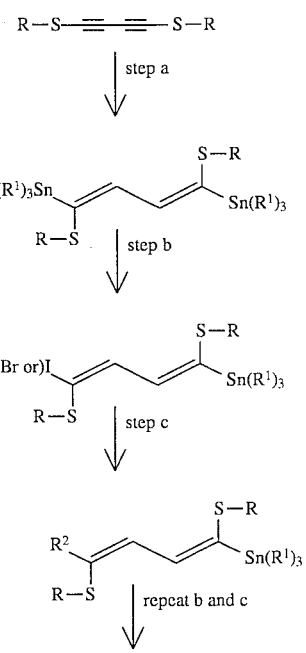

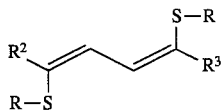

The method described above can be modified so as to produce symmetrically substituted 1,4-disulfurated-1,3-butadienes by carrying out the sequential steps of: (a) reacting a 1,4-disulfurated-1,3-butadiyne with a triaryl or trialkylstannane to form a 1,4-disulfurated-1,4-distannyl-1,3-butadiene; and (b) treating the resulting 1,4-disulfurated-1,4-distannyl-1,3-butadiene with at least 2 equivalents of iodine, bromine or chlorine to produce a 1,4-disulfurated-1,4-dihalo-1,3-butadiene. By this method one can prepare symmetrically substituted compounds of formula:

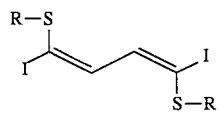

The method may include the additional step of treating the 1,4-disulfurated-1,4-dihalo-1,3-butadiene with a copper-palladium complex or a copper complex of a substituent residue whereby a 1,4-disulfurated-1,3-butadiene having the same substituent residue at positions 1 and 4 is formed. Compounds of formula:

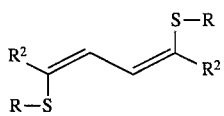

can arise from this method.

In another aspect the invention relates to a method for synthesizing a 3,6-disubstituted 1,2-dithiin comprising the sequential steps of: (a) reacting a sulfur-protected-1,4-dimercapto-1,3-butadiyne with triphenyltin hydride or trialkyltin hydride to form a 1,4-disulfurated-1,4-distannyl-1,3-butadiene; (b) treating the 1,4-disulfurated-1,4-distannyl-1,3-butadiene with iodine to produce a 1,4-disulfurated-1-iodo-4-stannyl-1,3-butadiene; (c) treating the 1,4-disulfurated-1-iodo-4-stannyl-1,3-butadiene with a copper-palladium complex or cuprate of a first substituent residue whereby a 1,4-disulfurated-4-stannyl-1,3-butadiene having the first substituent residue at position 1 is formed; (d) repeating each of steps (b) and (c) with a second substituent residue whereby a 1,4-disulfurated-1,3-butadiene having said the substituent residue at position 1 and the second residue at position 4 is formed; (e) cleaving all sulfur-protecting groups to produce a 1,4-dimercapto-1,3-butadiene having the first substituent residue at position 1 and the second residue at position 4; and (f) oxidatively cyclizing the 1,4-dimercapto-1,3-butadiene to produce a 3,6-disubstituted 1,2-dithiin.

The method can be illustrated schematically as shown:

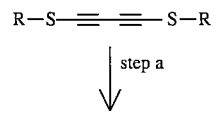

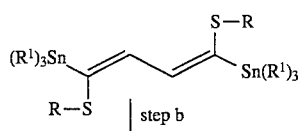

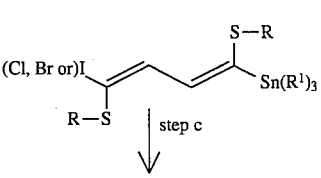

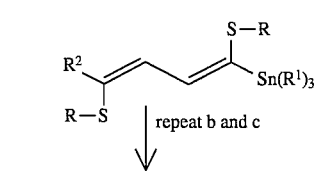

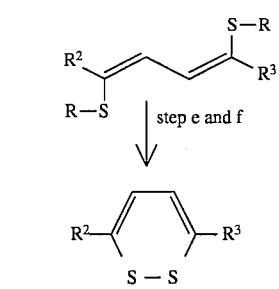

In one embodiment the first substituent residue ($R^2$) may be —C≡C—$R^5$, where $R^5$ is trialkylsilyl or a $C_1$ to $C_{10}$ hydrocarbon. In another embodiment the second substituent residue ($R^3$) may be —C≡C—$R^6$ where $R^6$ is trialkylsilyl or a $C_1$ to $C_{10}$ hydrocarbon.

When the sulfur-protected-1,4-dimercapto-1,3-butadiyne is 1,4-bis(benzylthio)-1,3-butadiyne, the protecting groups can be cleaved from the resulting 1,4-bis(benzylthio)-1,3-butadiene by treatment with lithium 1-N,N-dimethylaminonaphthalenide or lithium 4,4'-di-tert-butylbiphenyl. If desired, the 1,4-dimercapto-1,3-butadiene can be trapped with acetyl chloride or acetic anhydride and the resulting thioester can be hydrolyzed with an alkali metal hydroxide. This optional trapping of the dimercaptan as a bis(thioester) introduces extra steps, but may be of utility in some cases by allowing an extra opportunity for purification.

In another aspect, the invention relates to 1,4-disulfurated-1,3-butadienes of formula:

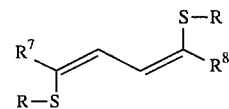

wherein $R^7$ is chosen from the group consisting of iodo, bromo, chloro, $(R^1)_3Sn$—, CH=CH—$R^{4a}$ and —C≡C—$R^{4a}$; $R^8$ is chosen from the group consisting of iodo, bromo, chloro, $(R^1)_3Sn$—, CH=CH—$R^{4b}$ and —C≡C—$R^{4b}$; and $R^{4a}$ and $R^{4b}$ are independently selected from the group consisting of trialkylsilyl and $C_1$ to $C_{10}$ hydrocarbons.

Preferred embodiments of the foregoing genus include: 1,4-disulfurated-1,3-butadienes wherein $R^7$ and $R^8$ are different; 1,4-disulfurated-1,3-butadienes wherein R is chosen from the group consisting of benzyl, p-methoxybenzyl, 2,6-dimethoxybenzyl, diphenylmethyl, triphenylmethyl, t-butyl, 2-(trimethylsilyl)ethyl and acetyl; 1,4-disulfurated-1,3-butadienes wherein $R^7$ and $R^8$ are both $(R^1)_3Sn$—; and 1,4-disulfurated-1,3-butadienes wherein $R^7$ is $(R^1)_3Sn$— and $R^8$ is iodine. A particularly preferred compound from this latter group is 1,4-bis(benzylthio)-1-iodo-4-(triphenylstannyl)-1,3-butadiene.

Other embodiments include 1,4-disulfurated-1,3-butadienes wherein $R^7$ is $(R^1)_3Sn$— and $R^8$ is —C≡C—$R^{4b}$ and 1,4-disulfurated-1,3-butadienes wherein $R^7$ is —C≡C—$R^{4a}$; $R^8$ is —C≡C—$R^{4b}$; and $R^{4a}$ and $R^{4b}$ are different.

In another aspect, the invention relates to a method as described above wherein, instead of reacting the 1,4-disulfurated-4-stannyl-1,3-butadiene having a first substituent residue at position 1 with iodine, bromine or chlorine to produce a 1,4-disulfurated-4-halo-1-substituted-1,3-butadiene, one treats the 1,4-disulfurated-4-stannyl-1,3-butadiene having a first substituent residue at position 1 with an organolithium compound to provide a 1,4-disulfurated-4-lithio-1,3-butadiene having a first substituent residue at position 1. To produce monosubstituted 1,2-dithiins one can then quench the 1,4-disulfurated-4-lithio-1,3-butadiene with a proton source (such as ammonium chloride) to provide a 1,4-disulfurated-1,3-butadiene having a single substituent residue at position 1. One could also replace the lithium by a substituent using chemistry well known in the art.

Alternatively one may treat the 1,4-disulfurated-4-stannyl-1,3-butadiene having a first substituent residue at position 1 with iodine to produce a 1,4-disulfurated-4-iodo-1-substituted-1,3-butadiene; and then treat the resulting 1,4-disulfurated-4-iodo-1-substituted-1,3-butadiene with an organolithium compound to provide a 1,4-disulfurated-4-lithio-1,3-butadiene having the substituent residue at position 1. This may also be quenched with a proton source to provide a 1,4-disulfurated-1,3-butadiene having a single substituent residue at position 1.

1,2-Dithiins, monosubstituted at the 3-position, may then be prepared by the sequential steps of: (a) reacting a sulfur-protected-1,4-dimercapto-1,3-butadiyne with triphenyltin hydride or trialkyltin hydride to form a 1,4-disulfurated-1,4-distannyl-1,3-butadiene; (b) treating the 1,4-disulfurated-1,4-distannyl-1,3-butadiene with iodine to produce a 1,4-disulfurated-1-iodo-4-stannyl-1,3-butadiene; (c) treating the 1,4-disulfurated-1-iodo-4-stannyl-1,3-butadiene with a copper-palladium complex or cuprate of a substituent residue whereby a 1,4-disulfurated-4-stannyl-1,3-butadiene having the substituent residue at position 1 is formed; (d) treating the 1-substituted-1,4-disulfurated-4-stannyl-1,3-butadiene with an organolithium reagent whereby a 1,4-disulfurated-4-lithio-1,3-butadiene is formed; (e) quenching the 1,4-disulfurated-4-lithio-1,3-butadiene with a proton source to provide a 1,4-disulfurated-1,3-butadiene having a substituent residue at position 1; (f) cleaving all sulfur-protecting groups from the 1,4-disulfurated-1,3-butadiene to produce a 1,4-dimercapto-1,3-butadiene having a substituent residue at position 1; and (g) oxidatively cyclizing the 1,4-dimercapto-1,3-butadiene to produce a 1,2-dithiin, monosubstituted at the 3-position.

DETAILED DESCRIPTION OF THE INVENTION

Formation of a 3,6-disubstituted 1,2-dithiin requires in the precursors the proper 1,4-(Z,Z) stereochemistry for the sulfur groups and the proper regiochemistry for the substituents. In all of the processes that are described below, it is necessary to remember that both the regiochemistry of 1,2,4,3-addition and the (Z,Z) stereochemistry are essential to the subsequent success in cyclizing the disulfurated butadiene. Only one of four possible 1,4-disulfurated-1,4-disubstituted butadienes will work:

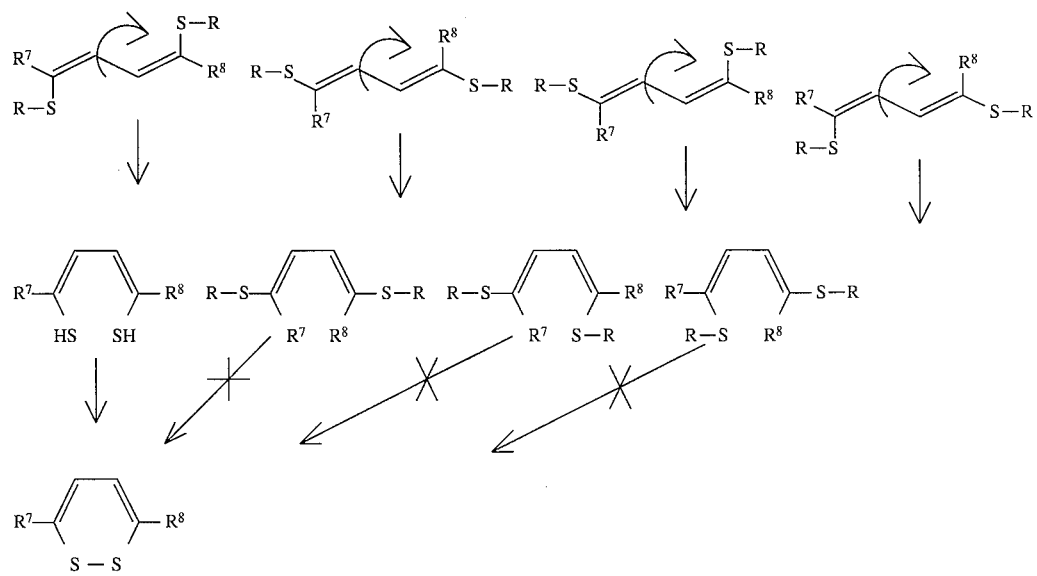

The starting material for the processes of the invention, 1,4-Bis(benzylthio)-1,3-butadiyne (3), was synthesized in 97% yield via Glaser oxidation of benzylthioethyne (2), in turn prepared in 96% yield by sequential treatment of timethylsilylethyne with n-butyllithium, sulfur, benzyl bromide and tetra-n-butylammonium fluoride (TBAF). Alternatively, 3 could be prepared in a one pot process in 52% yield from commercially available (Z)-1-methoxybut-1-en-3-yne by treatment with 3 equivalents of n-butyllithium, followed by thiolation and alkylation with benzyl bromide. If other protecting groups (than benzyl) are desired, the appropriate precursor can replace benzyl bromide. For the purpose of synthesizing dithiins, any of the protecting groups well-known in the art for protecting sulfur could be employed. It is only necessary that the group mask the SH functionality until the substituents adjacent the sulfurs have been elaborated, and then be capable of being removed to provide free mercapto groups (SH) without destroying the substituents. Thus, for example, p-methoxybenzyl, 2,6-dimethoxybenzyl, diphenylmethyl, triphenylmethyl, 2-(trimethylsilyl)ethyl or t-butyl could be used in place of the benzyl protecting group.

The processes of the invention are illustrated and exemplified as shown:

this case, a distinct advantage in purification. The hydrostannylation of acetylenes is known to be promoted by free radical initiators such as AIBN, as well as by trialkylborons and palladium complexes, and we have found that a mixture of palladium complex and triethylboron is particularly effective at maximizing the yield and minimizing the dimerization of the tin species, while still allowing 1,2,4,3 addition and production of butadienes with pure 1,4-(Z,Z)-sulfur substitution.

The formation of 4 from 3 would not have been predicted because alkyl- or trimethylsilyl-substituted 1,3-diynes are reported to undergo only monohydrostannation, and then with tin attaching itself to the 2 (or 4) position rather than the 1 (or 3) position.

Surprisingly, regio-differentiation is simply achieved by iododestannylation of 4 with 1.1 eq of iodine at 0° C. in methylene chloride for 3 hours, whereupon (E,E)-1,4-bis-(benzylthio)-1-iodo-4-triphenylstannyl-1,3-butadiene (5) is produced. Iodine was used to prepare the vinyl halide because it is easy to handle and provides a good leaving group, but, although iodine is preferred, there appears no reason that bromine or chlorine would not also function in the reaction. Interestingly, the addition of the first halogen (iodine) appears to deactivate the other double bond of the

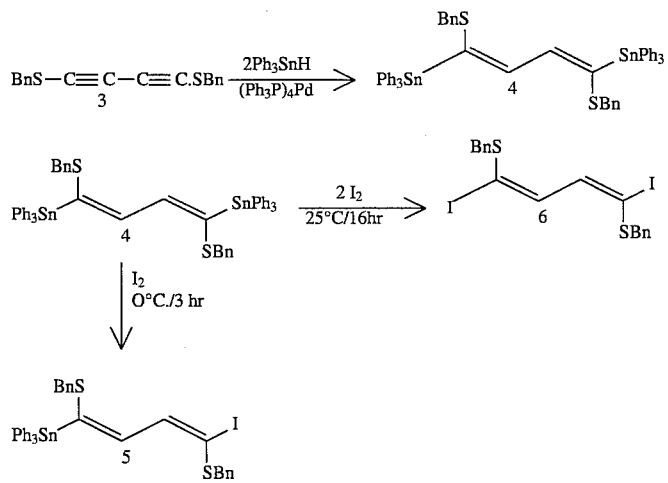

Treatment of the appropriately protected 1,4-sulfurated-1,3-butadiyne, in this case the benzyl-protected 3, with 2 equivalents of Ph₃SnH in the presence of (Ph₃P)₄Pd and triethylboron provides (E,E)-1,4-bis(benzylthio)-1,4-bis-(triphenylstannyl)-1,3-butadiene 4 as monoclinic crystals after overnight refrigeration of a hexane solution of the reaction concentrate. The triphenyltin hydride could be replaced with other tin hydrides, such as trimethyltin hydride or tributyltin hydride, but the product of the triphenyltin hydride addition is nicely crystalline and provides, in butadiene to replacement of the tin. Thus, conversion of 5 (or 4) to (E,E)-1,4-bis(benzylthio)-1,4-diiodo-1,3-butadiene 6 was slower, requiring overnight stirring.

The polyyne side chains are introduced by a series of Pd(II)-mediated coupling reactions which occur smoothly even in the case of 5, which contains both triphenylstannyl and iodo groups:

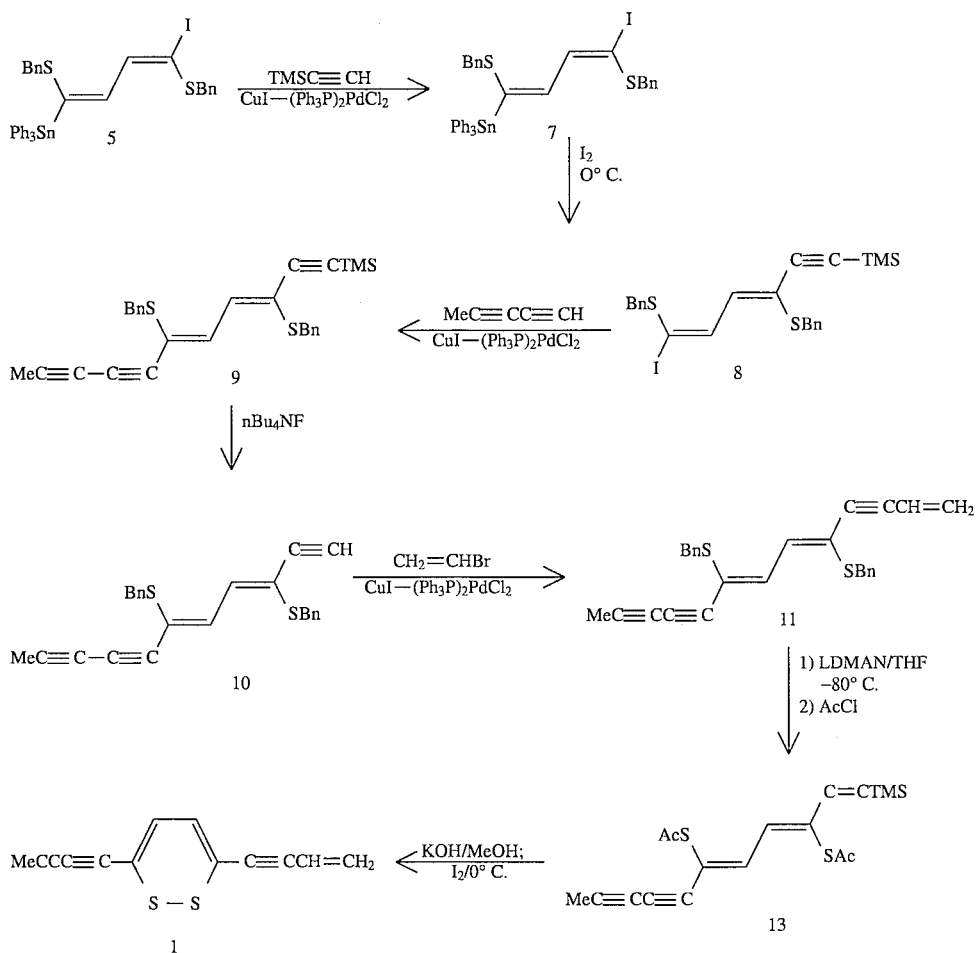

Thus, reaction of 5 with 1 equivalent of trimethylsilylethyne and CuI-(Ph₃P)₂PdCl₂ in benzene-diethylamine for 40 hours gave (E,E)-1,4-bis(benzylthio)-1-triphenylstannyl-6-(trimethylsilyl)hexa-1,3-diene-5-yne) 7. In the example shown, a Cu-Pd complex of an acetylene was used to displace the iodo substituent because the target is an acetylene-substituted 1,2-dithiin (thiorubrin B). If, however, one wished to synthesize an alkene or alkane-substituted 1,2-dithiin, one could use a copper-palladium complex of an alkene or an alkyl cuprate, respectively.

Because it may be of interest to introduce polar functionality into thiarubrine analogs, one could employ palladium or copper species containing ethers, esters, amides and similar functionalities, which could then be cleaved by well-known procedures to alcohols, carboxylic acids and amines, respectively, if desired. Moreover, because of the acidity of the acetylenic proton in 10 (below), one can introduce all manner of polar substituents that will ultimately be attached to the 1,2-dithiin through the acetylene. In addition, the lithiation chemistry described below allows wide latitude in the substituents that can be attached directly to the 1,2-dithiin ring via incorporation into the precursor.

Brief treatment of 7 with iodine in methylene chloride provides (E,Z)-1,4-bis(benzylthio)-1-iodo-6-(trimethylsilyl)hexa-1,3-diene-5-yne 8. As before, other halogens (bromine and chlorine) could be employed in place of iodine, but iodine is preferred because it is more convenient to work with and easier to displace. The ease of the reaction with iodine, once the triphenyltin has been replaced by the acetylenic residue, indicates that there is some apparent deactivation of the tin towards halogen replacement that arises from the presence of the first halogen on the C-4 carbon. One might hypothesize that this may be attributed to an electronic effect through conjugation, but applicants do not wish to be held to that speculative mechanism.

Reaction of 8 with 1,3-pentadiyne gave (Z,Z)-3,6-bis-(benzylthio)-1-(trimethylsilyl)undeca-3,5-diene-1,7,9-triyne 9 which, upon desilylation with TBAF, afforded (Z,Z)-3,6-bis(benzylthio)undeca- 3,5-diene-1,7,9-triyne 10. Reaction of this compound with vinyl bromide and CuI(Ph₃P)₂PdCl₂ gave (Z,Z)-5,8-bis-(benzylthio)trideca-1, 5,7-triene-3,9,11-triyne 11 as a yellow oil.

When symmetrically disubstituted butadienes are desired (e.g. for a 3,6-symmetrically disubstituted 1,2-dithiin), double Pd(II)-mediated coupling of diiodo compound 6 with a suitable substituent is possible. Thus coupling of diiodo compound 6 with trimethylsilylethyne affords symmetrical (Z,Z)-1,8-bis(trimethylsilyl)-3,6-bis(benzylthio)octa-3,5-diene-1,7-diyne 12.

When the sulfur-protecting group is benzyl, deprotection may prove difficult due to the high reactivity of the polyyne functionalities. In this case, other protecting groups can be considered, or particular conditions for the selective removal of the benzyl can be devised. In the examples below, the latter course was chosen. Model studies showed that (Z,Z)-1,4-bis(benzylthio)-1,3-butadiene (13), prepared in 78% yield by refluxing sodium benzylthiolate with 1,4-bis(trimethylsilyl)-1,3-butadiene in MeOH for 48 hours, on treatment with lithium 1-(Z,Z)-dimethylaminonaphthalenide (LDMAN) followed by acetyl chloride gave (Z,Z)-1,4-bis(acetylthio)-1,3-butadiene (14) in 96% yield (yields of 14 were lower when 13 was cleaved with Na/NH$_3$). This, on sequential treatment with KOH/MeOH followed by iodine, gave 1,2-dithiin in 73% yield. In a similar manner, (Z,Z)-1,4-bis(benzylthio)-1,4-diphenyl-1,3-butadiene on sequential treatment with LDMAN and acetyl chloride gave (Z,Z)-1,4-bis(acetylthio)- 1,4,diphenyl-1,3-butadiene, in 48% yield. Similarly, 11 was treated with LDMAN in THF at −80° C. for 1.5 h and the reaction quenched with excess acetyl chloride to give (Z,Z)-5,8-bis(thioacetyl)trideca-1,5,7-triene-3,9,11-triyne (15) which, after chromatography, was cleaved with methanolic KOH, oxidized at low temperature with iodine, and purified by chromatography, giving thiarubrine B (1) in 17% overall yield from 11. The spectroscopic properties of 1 (EI-MS, UV, $^1$H NMR and $^{13}$C NMR) matched those reported and those determined by us for natural 1.

As an alternative to the process described above, one can react the distannyl compound 4 or the iodobutadiene 5 or 8 with an alkyllithium and generate a vinyllithium species in which the lithium can be replaced by a wide variety of electrophilic species by procedures well known in the art for reactions of vinyllithium reagents. By this means one could introduce, for example, a carboxylate (via ClCOOEt), an aldehyde (via DMF addition), an alcohol (via aldehyde addition), or even a hydroxy-ether (via ethylene oxide addition), all directly attached to the ultimate 1,2-dithiin.

EXAMPLES 1,4-Bis(benzylthio)-1,3-butadiyne (3). Method A. A solution of (Z)-1-methoxy-1-buten-3-yne (20 g, 2.44 mmol) in THF (8 mL) under argon was cooled to −30° C. A solution of n-BuLi (2.5 M in hexanes, 3 mL, 7.5 mmol) was added dropwise. After stirring at −25° C. for 1 h, a gray-brown suspension was formed. The mixture was cooled to −70° C., then diluted with dry ether (10 mL). Sulfur powder (0.16 g, 5.0 mmol) was poured into the flask quickly. The suspension turned into a dark brown solution upon warming to −20° C. Benzyl bromide (0.88 mL, 0.73 mmol) was added to quench the reaction. The resulting solution was stirred at room temperature overnight. Ether (35 mL) and water (20 mL) were added, the ether layer was separated, and the aqueous layer was extracted by ether (2×20 mL). The combined organic layers were washed with NH$_4$Cl solution (2×15 mL), brine (1×10 mL) and water (1×10 mL), dried (MgSO$_4$), and concentrated in vacuo. The crude oil was purified by flash column chromatography (1:9 CH$_2$Cl$_2$:hexanes). A pale yellow solid (3) was obtained (0.37 g, 52%): mp 38°–39° C.; GC-EI-MS m/z 294 (M+); IR 2075 cm$^{-1}$; $^1$H NMR δ 1.2–7.41 (m, 10H), 3.96 (s, 4 H); $^{13}$C NMR δ 135.99, 129.07, 128.79, 128.05, 82.43, 74.22, 40.98; Anal. Calcd for C$_{18}$H$_{14}$S$_2$, C, 73.43; H, 4.79. Found, C, 73.46; H, 4.86.

Method B. To a solution of trimethylsilylacetylene (10 mL, 71 mmol) in ether (100 mL) under argon at −78° C. was slowly added n-BuLi (2.5 M in hexanes, 28.3 mL, 71 mmol). The solution was warmed to −20° C. and then cooled to −70° C. Sulfur powder (2.3 g, 72 mmol), in a flask connected to the reaction vessel by Gooch tubing, was poured into the reaction mixture. The mixture was warmed to 10° C., becoming a pale yellow solution. Benzyl bromide (8.5 mL, 72 mmol) was added to quench the reaction. The resulting solution was stirred overnight. The solution was quenched by addition of saturated NH$_4$Cl solution (30 mL), and the mixture was extracted with ether (3×50 mL), the combined ether layers washed with brine (1×30 mL) and water (1×30 mL). The organic phase was dried (MgSO$_4$) and concentrated in vacuo affording a yellow oil (16.5 g; 100%): GC EI-MS: 220 (M+). Without further purification a solution of this yellow oil (16.5 g, 72 mmol) in THF (150 mL) was treated with water (10 mL) followed by THF solution (100 mL) of tetra-n-butylammonium fluoride (TBAF; 1.1 eq). The resulting reddish brown solution was stirred for 2.5 h, and then washed with brine (3×50 mL), dried (MgSO$_4$, concentrated in vacuo, and distilled (39°–42° C./0.015 mmHg) affording benzylthioacetylene (2) as a yellow oil (10 g, 96%): $^1$H NMR (acetone-d$_6$) δ 7.5–7.25 (m, 5 H) 4.05 (s, 2 H) 3.38 (s, 1 H); $^{13}$C NMR (acetone-d$_6$ δ 137.89, 129.93, 129.38, 128.56, 85.43, 74.82, 40.07; IR 2041, 3286 cm$^{-1}$. A mixture of CuCl (0.27 g), TMEDA (0.41 mL) and acetone (40 mL) were placed in a three-necked flask, and with stirring O$_2$ was bubbled through the dark green solution for a few minutes. Compound 2 (8 g, 60 mmol) was added dropwise to the stirred green solution which was maintained at room temperature with a water bath. After 3 h, acetone was removed in vacuo and ice cold HCl solution (0.3 mL conc HCl diluted to 50 mL) was added to the concentrate. The suspension was extracted with ether (1×100, 2×50 mL). The combined ether layers were washed with brine (2×50 mL) and water (1×35 mL), dried (MgSO$_4$), and concentrated in vacuo affording 3 as a yellow solid (7.7 g, 97%).

(E,E)-1,4-Bis(benzylthio)-1,4-bis(triphenylstannyl)-1,3-butadiene (4). Tetrakis (triphenylphosphine)palladium (0.41 g, 0.35 mmol) was added to a benzene solution (250 mL) of 3 (5 g, 17 mmol) under argon. The solution was cooled to 5° C. Triphenyltin hydride (9.2 mL, 35 mmol) was introduced slowly by syringe. The solution was warmed to room temperature and stirred overnight and then concentrated in vacuo. Hexanes (100 mL) was added to the concentrate and the flask was stored at 0° C. overnight. Compound 4 in the form of a pale yellow solid was thus obtained (6 g, 36%): mp 157°–159° C., $^1$H NMR δ 6.8–7.7 (m, 42 H), 3.68 (s, 4 H); $^{13}$C NMR δ 136–141 (several), 126–129.5 (several), 40.54; Anal. Calcd for C$_{54}$H$_{46}$S$_2$Sn$_2$, C, 65.10; H, 4.62. Found, C, 65.08; H, 4.77.

The preceding reaction was repeated using slightly different conditions. Tetrakis(triphenylphosphine)palladium (0.01 g, 0.009 mmol) was added to a toluene solution (10 mL) of 1,4-bis(benzylthio)-1,3-butadiyne (2) (0.125 g, 0.43 mmol) under argon. The solution was cooled to −30° C. A hexane solution of triethylborane (0.1 mL of 1 M solution, 0.1 mmol) was added followed by slow addition (by syringe) of triphenyltin hydride (0.371 g, 1.06 mmol) in hexane (6 mL). The solution was warmed to room temperature and stirred overnight and then concentrated in vacuo. As before, hexanes (5 mL) was added to the concentrate and the flask was stored at 0° C. overnight. An improved yield of compound 3 was thus obtained (0.238 g, 56%): mp 157°–159° C.

Colorless crystals of (E,E)-1,4-bis(benzylthio)-1,4-bis-(triphenylstannyl)-1,3-butadiene 4 were obtained by slow evaporation of a CH$_2$Cl$_2$-hexane solution. A well-shaped crystal was mounted on the end of a glass fiber. Intensity data was measured on a Nicolet (Siemens) R3m four-circle diffractometer equipped with a graphite monochromator, using Mo-K$_\alpha$ radiation (λ=0.71073 Å) at 298 K. Data were corrected for background, attenuators, Lorentz and polarization effects in the usual fashion, but not for absorption. The solution of the structure was consistent with the structure proposed above.

(E,E)-1,4-Bis(benzylthio)-1,4-diiodo-1,3-butadiene (6). Iodine (122 mg, 0.48 mmol) in $CH_2Cl_2$ (3 mL) was added over a period of 1.5 h at 0° C. to 4 (200 mg, 0.20 mmol) in $CH_2Cl_2$ (9 mL) under argon. The solution was warmed to room temperature and stirred overnight. Analysis by TLC (1:3 $CH_2Cl_2$:hexanes) indicated the disappearance of 4. The solution was washed with $NaHSO_3$ (2×20 mL), and KF solutions (1×20 mL), dried ($MgSO_4$), concentrated in vacuo, and purified by flash column chromatography (1:6 $CH_2Cl_2$:hexanes) to give a pale yellow solid (6) (110 mg, 0.20 mmol, 100% yield): mp 111°–112° C.; $^1$H NMR δ 7.20–7.35 (m, 10 H), 7.17 (s, 2 H), 3.85 (s, 4 H); $^{13}$C NMR δ 145.25, 136.36, 129.18, 128.63, 127.69, 95.10, 42.77; Anal. Calcd for $C_{18}H_{16}I_2S_2$, C, 39.29; H, 2.93. Found, C, 39.50; H, 3.13.

(E,E)-1,4-Bis(benzylthio)-1-iodo-4-triphenylstannyl-1,3-butadiene (5). Iodine (56 mg, 0.22 mmol) in $CH_2Cl_2$ (10 mL) was added over a period of 2 h at 0° C. to 4 (200 mg, 0.20 mmol) in $CH_2Cl_2$ (20 mL) under argon. Analysis by TLC (1:2 $CH_2Cl_2$:hexanes) indicated the disappearance of 4. The solution was slowly warmed to room temperature and then washed with $NaHSO_3$ (2×25 mL) and KF solution (1×25 mL), dried ($MgSO_4$), concentrated in vacuo and the residue purified by flash column chromatography (1:6 $CH_2Cl_2$:hexanes) to afford 5 as a pale yellow oil (0.15 g, yield 97%): $^1$H NMR δ 6.6–7.8 (m, 27 H), 3.78 (s, 2 H), 3.75 (s, 2 H); $^{13}$C NMR δ 127–146 (several), 42.24, 40.46; Anal. Calcd for $C_{36}H_{31}IS_2Sn$, C, 55.91; H, 4.04. Found, C, 56.12; H, 4.19.

(Z,Z)-1,8-Bis(trimethylsilyl)-3,6-bis(benzylthio)octa-3,5-diene-1,7-diyne (12). A mixture of CuI (4.7 mg. 0.02 mmol), bis(triphenylphosphine) palladium (II) chloride (7.7 mg, 0.01 mmol), $Et_2NH$ (2 mL), trimethylsilylethyne (80 mL, 0.546 mmol), 6 (100 mg, 0.182 mmol), and dry benzene (1.5 mL) was stirred for 48 h at room temperature under argon in a flask wrapped with aluminum foil. Analysis by TLC (1:4 $CH_2Cl_2$:hexanes) indicated the disappearance of starting compound. The solution was concentrated in vacuo, and water (10 mL) and ether (25 mL) were added to the residue. The layers were separated, the aqueous layer was extracted with ether (2×10 mL), the combined ether layers were washed with water (2×10 mL), dried ($MgSO_4$), and concentrated in vacuo. Flash column chromatography of the residue (2.5:97.5 ethyl acetate: hexanes) afforded 12 as a pale yellow solid (63.3 mg, yield 71%): $^1$H NMR δ 7.2–7.5 (m, 12 H), 6.97 (s, 2 H), 4.15 (s, 4 H), 0.25 (s, 18 H); $^{13}$C NMR δ 137.76, 131.83, 128.92, 128.58, 128.27, 121.15, 102.43, 101.78, 37.37, –0.09; Anal. Calcd for $C_{28}H_{34}S_2Si_2$, C, 68.51; H, 6.98. Found, C, 68.57; H, 7.02.

(E,E)-1,4-Bis(benzylthio)-1-triphenylstannyl-6-(trimethylsilyl)hexa-1,3-diene-5-yne (7). A mixture of $EtNH_2$ (1 mL) and trimethylsilylethyne (32 mL, 0.23 mmol) were added to a solution of 5 (0.148 g, 0.190 mmol), CuI (1.81 mg., 0.0095 mmol) and $(Ph_3P)_2PdCl_2$ (6.67 mg, 0.0095 mmol) in benzene (3 mL) under argon. The resulting yellow-green solution was stirred at room temperature for 38 h, and then concentrated in vacuo. The residue was mixed with ether (20 mL) and water (5 mL), the layers were separated and the aqueous layer was extracted by ether (2×10 mL). The combined ether layers were washed with $NH_4Cl$ solution (2×25 mL) and water (10 mL), dried ($MgSO_4$), and concentrated in vacuo. Flash column chromatography (1:6 $CH_2Cl_2$:hexanes) of the dark, oily residue gave 7 as a yellow solid (122 mg, yield 86%): mp 122°–123° C.; $^1$H NMR δ 6.9–7.8 (m, 27 H), 4.06, 37.27, 0.03; Anal. Calcd for $C_{41}H_{40}S_2SiSn$, C, 66.21; H, 5.42. Found, C, 66.42; H, 5.55.

(E,Z)-1,4-Bis(benzylthio)-1-iodo-6-(trimethylsilyl)hexa-1,3-diene-5-yne (8). Iodine (36 mg, 0.14 mmol) in $CH_2Cl_2$ (8 mL) was added over a period of 2 h at 0° C. to 7 (85 mg, 0.114 mmol) in $CH_2Cl_2$(12 mL) under argon. Analysis by TLC (1:6$CH_2Cl_2$:hexanes) indicated the disappearance of 7. The solution was warmed to room temperature, washed with $NaHSO_3$ (2×20 mL) and KF (10 mL) solutions, dried ($MgSO_4$), concentrated in vacuo, and the residue purified by flash column chromatography (1:4 $CH_2Cl_2$:hexanes) to give 8 as a yellow solid (56.4 mg, 95% yield): $^1$H NMR δ 7.52 (d, J=10.5 Hz, 1 H), 7.2–7.4 (m, 10 H), 6.74 (d, J=10.5 Hz, 1 H), 4.11 (s, 2 H), 3.97 (s, 2 H), 0.27 (s, 9 H); $^{13}$C NMR δ 143.93, 136.42, 132.89, 129.20, 128.60, 127.62, 127.34, 120.75, 101.91, 95.48, 43.28, 37.36, –0.08; Anal., Calcd for $C_{23}H_{25}IS_2Si$, C, 53.07; H, 4.84. Found C, 53.27; H, 5.00.

(Z,Z)-3,6-Bis(benzylthio)-1-(trimethylsilyl)undeca-3,5-diene-1,7,9-triyne (9). To a DMF (5 mL) solution of 1-trimethylsilyl-1,3-pentadiyne (0.4 g, 2.94 mmol) under argon was added TBAF (0.8 g, 3 mmol) and several drops of water. The dark brown solution was stirred for 2 h at room temperature, then diluted with benzene (3 mL). The benzene layer was washed with saturated brine (5×5 mL). After drying ($MgSO_4$) and filtering, the solution was transferred to a flask containing 8 (500 mg, 0.96 mmol), $(Ph_3P)_2PdCl_2$ (34 mg, 0.048 mmol), CuI (9 mg, 0.048 mmol) and $Et_2NH$ (1 mL). The mixture was stirred under argon at room temperature for 40 h, and then concentrated in vacuo. Ether (100 mL) and water (25 mL) were added, the layers were separated, the ether layer was washed with brine (3×20 mL), dried ($MgSO_4$), concentrated in vacuo and the residue purified by flash column chromatography (1:6 $CH_2Cl_2$:hexanes) giving 9 as a yellow oil (0.25 g, 57% yield): $^1$H NMR δ 7.15–7.3 (m, 10 H), 6.99 (d, J=11.7 Hz, 1 H), 6.90 (d, J=11.7 Hz, 1 H), 4.09 (s, 2 H), 4.06 (s, 2 H), 1.98 (s, 3 H), 0.20 (s, 9 H); $^{13}$C NMR δ 120–138 (several), 102.32 102.09, 84.37, 80.86, 72.45, 64.35, 37.36, 37.27, 4.82, –0.200.

(Z,Z)-3,6-Bis(benzylthio)undeca-3,5-diene-1,7,9-triyne (10). Under argon, a solution of TBAF (152 mg, 0.482 mmol) in THF (2 mL) was added to a solution of 5 (200 mg, 0.438 mmol) in THF (5 mL) in a flask protected from light with aluminum foil. After stirring at room temperature for 3 h, the solution was diluted with $CH_2Cl_2$(30 mL), washed with brine (3×20 mL), dried ($MgSO_4$) and the residue purified by flash column chromatography (1:6 $CH_2Cl_2$:hexanes) to afford 10 as a yellow oil (145 mg, 86% yield): $^1$H NMR δ 7.1–7.21 (m, 10 H), 6.92 (s, 2 H), 4.02 (s, 2 H), 4.00 (s, 2 H), 3.32 (s, 1 H), 1.93 (s, 3 H); $^{13}$C NMR δ 120–138 (several), 84.47, 83.33, 81.71, 80.92, 72.32, 64.31, 37.38, 37.35, 4.84.

(Z,Z)-5,8-Bis(benzylthio)trideca-1,5,7-triene-3,9,11-triyne (11). Vinyl bromide (0.5 mL, excess) was condensed into a flask under argon, followed by addition of CuI (7.2 mg, 0.015 mmol), $(Ph_3P)_2PdCl_2$(26 mg, 0.0376 mmol) and $Et_2NH$ (3 mL). Compound 10 (145 mg, 0.376 mmol) in benzene (10 mL) was added at 5° C. and the mixture was stirred in the dark for 16 h. Benzene was removed in vacuo, the residue was dissolved in $CH_2Cl_2$ (10 mL), washed with $NH_4Cl$ solution (2×15 ml) and water (15 mL), dried ($MgSO_4$), concentrated in vacuo, and the residue purified by flash column chromatography (1:5 $CH_2Cl_2$:hexanes) giving 11 as a yellow-green oil (109 mg, yield 70%): EI-MS, m/z 410 (M+), $NH_3$ CI-MS, m/z 428 ($MNH_4$+); UV ($CH_2Cl_2$) $λ_{max}$ 403; IR ($CH_2Cl_2$) 2226 (m), 2193 (w), 2142 (w) (all C≡C), 1602 (m, C=C) $cm^{-1}$; $^1$H NMR δ 7.1–7.3 (m, 10H), 6.95 (d, J=17.7, 2.1 Hz, 1 H), 5.49 (dd, J=11.1, 2.1 Hz, 1 H), 4.03 (s, 2 H), 4.02 (s, 2 H), 1.96 (s, 3 H); $^{13}$C NMR δ

116–138 (several), 94.90, 88.69, 84.46, 80.94, 72.69, 64.46, 37.52, 4.99.

(Z,Z)-5,8-Bis(thioacetyl)trideca-1,5,7-triene-3,9,11-triyne (13). Li ribbon (6.5 mg, 0.94 mmol) was suspended in THF (3.5 mL) at −55° C. and 1-N,N-dimethylaminonaphthalene (170 mg, 0.16 mL, 0.99 mmol) was added slowly. After 5 min, the solution became dark green. The green solution was stirred for 4 h, then cooled to −85° C. for 15 min. Compound 11 (80 mg, 0.19 mmol) in THF (2.5 mL) was introduced slowly over a period of 2 h using a syringe pump. The resulting dark brown solution was stirred for 1.5 h and then quenched by addition of several drops of absolute MeOH. Acetyl chloride (1 mL, excess) was added carefully, the solution was warmed slowly to room temperature and stirred for 15 min, and concentrated in vacuo. Small portions of CH$_2$Cl$_2$ and water were used to rinse the residue into a separatory funnel and the aqueous layer was extracted with ether (2×15 mL). The combined organic layers were washed with HCl solution (10%, 3×10 mL) and brine (2×10 mL), dried (MgSO$_4$), and concentrated in vacuo to a brown liquid (170 mg), which was purified by flash column chromatography (1:9 ethyl acetate:hexanes) to give 13 as a reddish solid (35 mg, R$^f$ 0.20) which was used directly in the subsequent step.

3-(3-Buten-1-ynyl)-6-(1,3-pentadiynyl)-1,2-dithiin (Thiarubrine B, 1). The following experiment was done with complete exclusion of light. A small piece of KOH was added to a solution of compound 13 (35 mg) in absolute MeOH (4 mL) at 0° C. The solution was stirred until it turned red, whereupon iodine (40 mg, 0.16 mmol) in methanol (2 mL) was added slowly at −35° C. The dark solution was stirred for 20 min and then partitioned between pentane-ether (4:1 v/v, 30 mL) and water (20 mL). The aqueous layer was extracted with ether (2×15 mL), the combined organic layers were washed with diluted Na$_2$S$_2$O$_3$ solution (3×10 mL) and brine (4×10 mL), dried (MgSO$_4$), concentrated in vacuo, and the residue purified by flash column chromatography (hexanes) to afford thiarubrine B (1) as a red oil (7.5 mg; two step overall yield 17%): EI-MS, m/z 228 (M+); UV λ$_{max}$ (ethanol 342, 486; $^1$H NMR δ 2.05 (s, 3 H), 5.61 (dd, J=11.2, 2.0 Hz, 1 H), 5.75 ((dd, J=17.5, 2.0 Hz, 1 H), 5.99 (dd, J=17.5, 11.2 Hz, 1 H), 6.57 (d, J=6.9 Hz, 1 H), 6.66 (d, J=6.9 Hz, 1 H).

While the invention has been particularly shown and described with reference to preferred embodiments thereof, it will be understood by those skilled in the art that other changes in form and details may be made therein without departing from the spirit and scope of the invention.

We claim:

1. A 1,4-disulfurated-1,3-butadiene of formula:

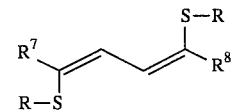

wherein

R is chosen from the group consisting of benzyl, p-methoxybenzyl, 2,6-dimethoxybenzyl, diphenylmethyl, triphenylmethyl, t-butyl, 2-(trimethylsilyl)ethyl and acetyl;

R$^7$ is chosen from the group consisting of iodo, bromo, chloro, (R$^1$)$_3$Sn—, CH═CH—R$^{4a}$ and —C≡C—R$^{4a}$;

R$^8$ is chosen from the group consisting of iodo, bromo, chloro, (R$^1$)$_3$Sn—, CH═CH—R$^{4b}$ and —C≡C—R$^{4b}$;

R$^1$ is alkyl of 1 to 4 carbons or phenyl; and

R$^{4a}$ and R$^{4b}$ are independently selected from the group consisting of trialkylsilyl and C$_1$ to C$_{10}$ hydrocarbons.

2. A 1,4-disulfurated-1,3-butadiene according to claim 1 wherein R$^7$ and R$^8$ are different.

3. A 1,4-disulfurated-1,3-butadiene according to claim 1 wherein R$^7$ and R$^8$ are both (R$^1$)$_3$Sn—.

4. A 1,4-disulfurated-1,3-butadiene according to claim 1 wherein R$^7$ is (R$^1$)$_3$Sn— and R$^8$ is iodine.

5. 1,4-Bis(benzylthio)-1-iodo-4-(triphenylstannyl)-1,3-butadiene according to claim 4.

6. A 1,4-disulfurated-1,3-butadiene according to claim 1 wherein R$^7$ is (R$^1$)$_3$Sn— and R$^8$ is —C≡C—R$^{4b}$.

7. A 1,4-disulfurated-1,3-butadiene according to claim 1 wherein R$^7$ is —C≡C—R$^{4a}$; R$^8$ is —C≡C—R$^{4b}$; and R$^{4a}$ and R$^{4b}$ are different.

* * * * *

UNITED STATES PATENT AND TRADEMARK OFFICE
CERTIFICATE OF CORRECTION

PATENT NO. : 5,478,959
DATED : Dec. 26, 1995
INVENTOR(S) : Block et al.

It is certified that error appears in the above-indentified patent and that said Letters Patent is hereby corrected as shown below:

Column 11, delete the first section of the structure:

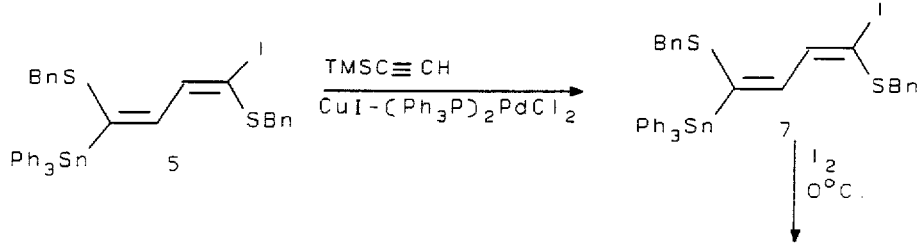

and insert therefor

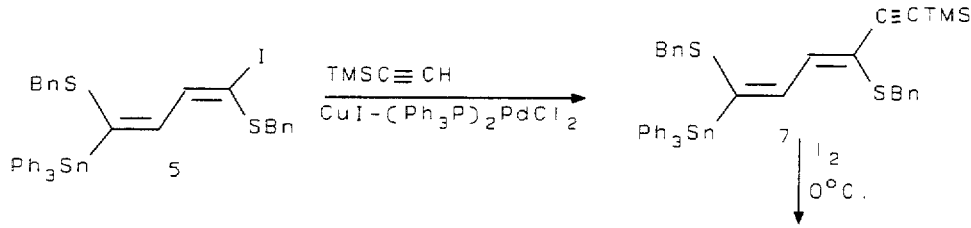

Signed and Sealed this

Twenty-eighth Day of May, 1996

*Attest:*

BRUCE LEHMAN

*Attesting Officer*  *Commissioner of Patents and Trademarks*